(12) United States Patent
Johnson

(10) Patent No.: US 8,162,905 B2
(45) Date of Patent: Apr. 24, 2012

(54) DELIVERY SYSTEM

(75) Inventor: Eric Gerard Johnson, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 669 days.

(21) Appl. No.: 11/016,530

(22) Filed: Dec. 17, 2004

(65) Prior Publication Data

US 2006/0135990 A1 Jun. 22, 2006

(51) Int. Cl.
*A61M 25/00* (2006.01)
(52) U.S. Cl. ........................................................ 604/284
(58) Field of Classification Search .................. 604/239, 604/284, 107, 164.01, 166.01, 198, 533–536
See application file for complete search history.

(56) References Cited

U.S. PATENT DOCUMENTS

| | | | |
|---|---|---|---|
| 3,399,674 A * | 9/1968 | Pannier et al. | 604/165.04 |
| 4,099,528 A * | 7/1978 | Sorenson et al. | 604/44 |
| 5,108,420 A | 4/1992 | Marks | 606/213 |
| 5,255,690 A | 10/1993 | Keith et al. | 128/772 |
| 5,290,222 A * | 3/1994 | Feng et al. | 604/86 |
| 5,334,217 A * | 8/1994 | Das | 606/213 |
| 5,651,776 A | 7/1997 | Appling et al. | 604/283 |
| 5,879,366 A | 3/1999 | Shaw et al. | 606/213 |
| 6,080,182 A | 6/2000 | Shaw et al. | 606/213 |
| 6,234,971 B1 | 5/2001 | Jang | 600/462 |
| 6,332,633 B1 | 12/2001 | Fitoussi et al. | 285/332 |
| 6,363,273 B1 * | 3/2002 | Mastrorio et al. | 600/434 |
| 6,699,233 B2 | 3/2004 | Slanda et al. | 604/533 |
| 2003/0139819 A1 * | 7/2003 | Beer et al. | 623/23.71 |

FOREIGN PATENT DOCUMENTS

| | | |
|---|---|---|
| EP | 0 282 143 | 1/1988 |
| EP | 0 388 112 | 3/1990 |
| WO | WO 2004/082753 | 9/2004 |

* cited by examiner

*Primary Examiner* — Kevin C Sirmons
*Assistant Examiner* — Bradley Osinski
(74) *Attorney, Agent, or Firm* — Andrea W. Burke

(57) ABSTRACT

Novel delivery systems suitable for delivering, for example, implantable devices. Delivery system comprises a three-catheter system in conjunction with at least one floating connector. Delivery system may be particularly suitable for delivering septal occlusion devices to a patient's heart.

13 Claims, 9 Drawing Sheets

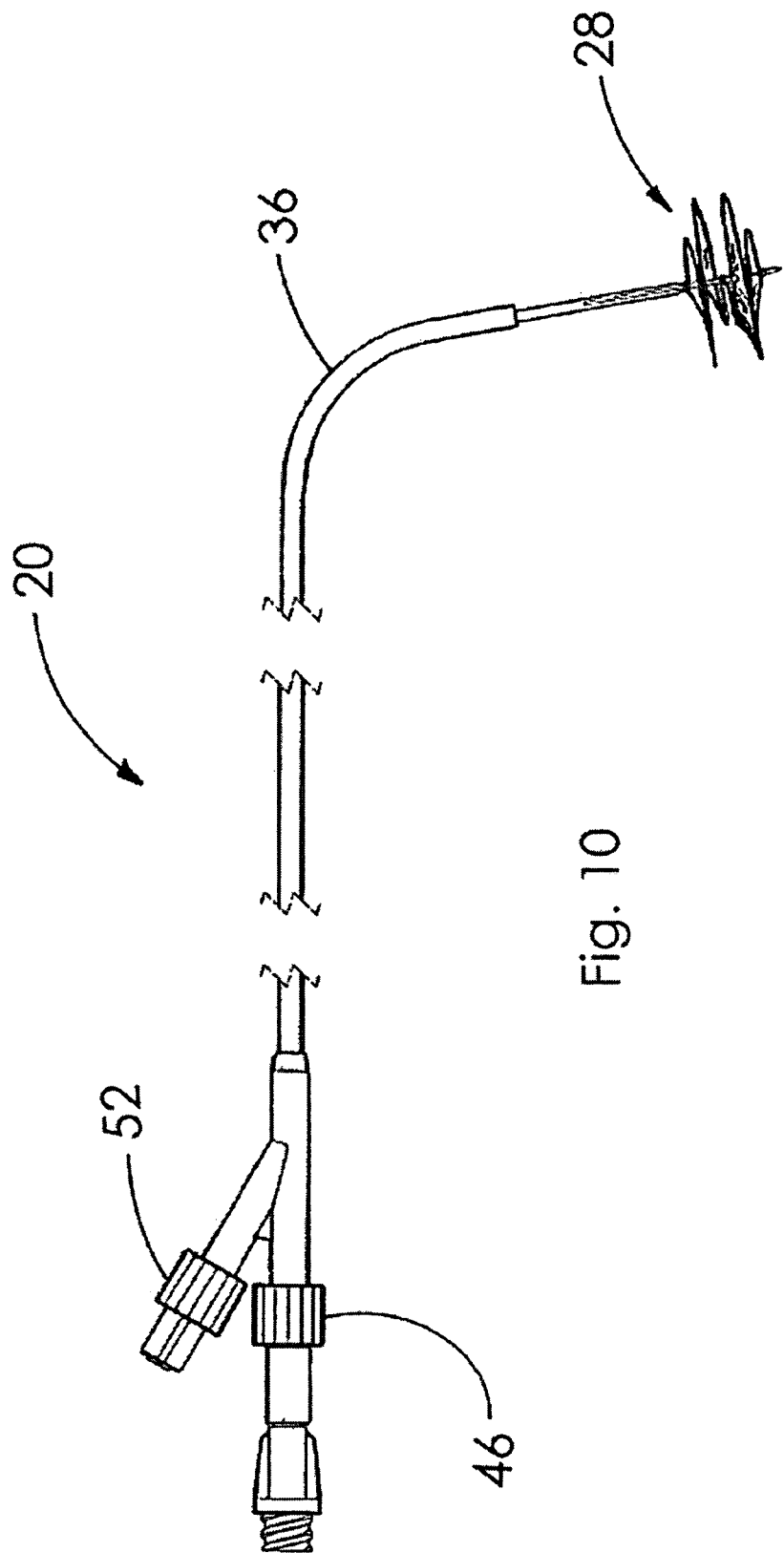

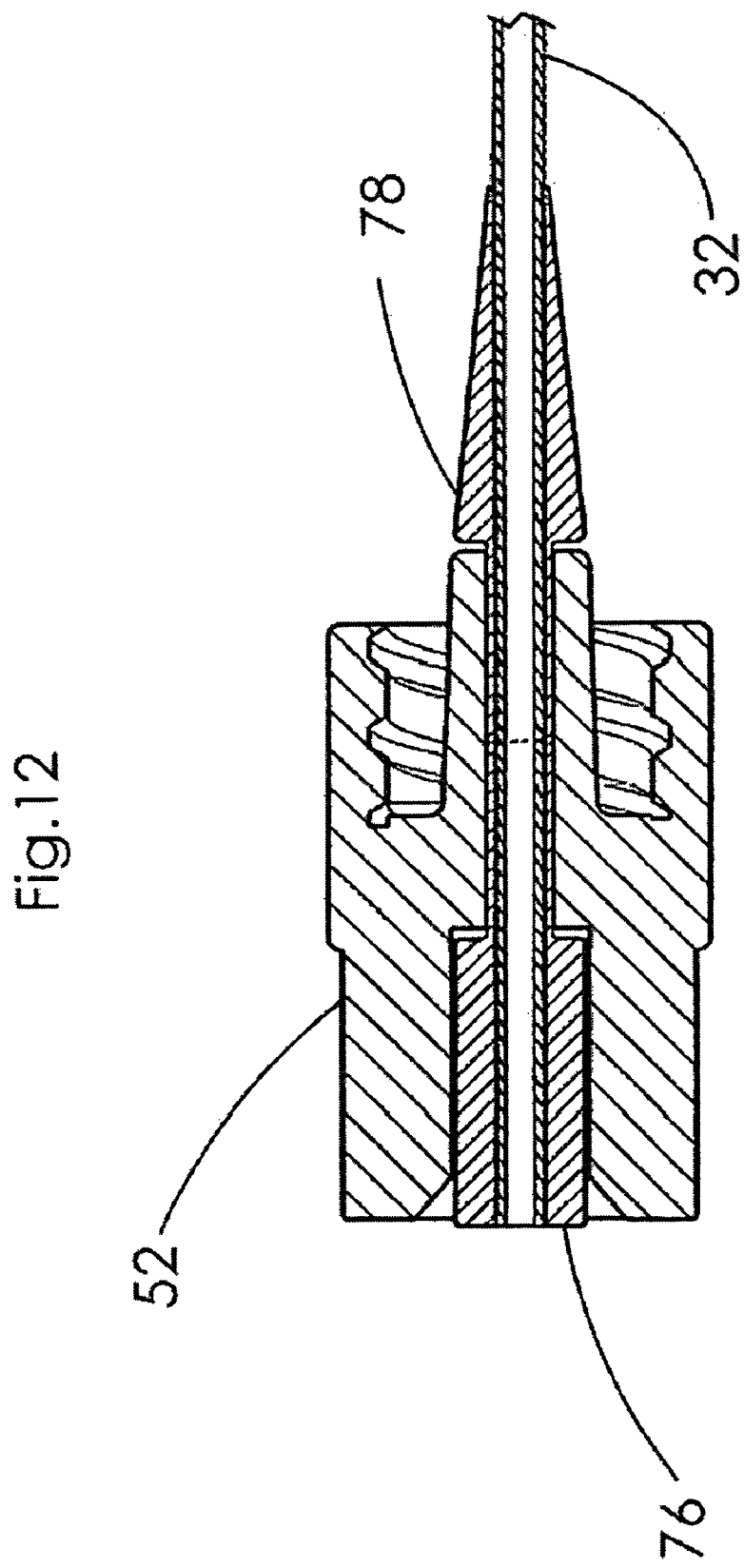

DELIVERY SYSTEM

FIELD OF THE INVENTION

The invention relates to catheter delivery systems useful for delivering, for example, implantable devices.

BACKGROUND OF THE INVENTION

Various catheter-based delivery systems require sequential "push-pull" motions to deploy or position a medical device. For example, a commercially available occluder device, referred to as HELEX™ septal occluder (W. L. Gore & Associates, Flagstaff, Ariz.), requires a series of push-pull manipulations of the delivery system components to deliver and deploy the septal occlusion device. During the deployment sequence a user must hold or fix one catheter component while simultaneously manipulating a second catheter component. The current delivery system used to deploy the HELEX™ septal occluder has three catheter components, essentially co-axially arranged along its entire length and independently movable with respect to each other. At specific stages of the push-pull delivery sequence the hand-held coaxial catheter components can become separated by extended distances resulting in repeated and lengthy hand motions.

Such a septal occluder, suitable delivery systems, and methods for delivering the septal occluder are described in detail in commonly owned U.S. Pat. No. 6,080,182.

SUMMARY OF THE INVENTION

Disclosed are novel delivery systems comprising: a first catheter shaft having a proximal end and a distal end, the proximal end having at least first and second openings, the distal end having at least one opening, and a lumen extending from the distal end opening to the at least first and second proximal end openings; a second catheter shaft having a proximal end and a distal end, at least a portion being located within the first catheter shaft lumen and extending from the first proximal end opening to the distal end opening, the second catheter shaft having a lumen extending from a distal end opening to at least a side opening in the second catheter shaft located between the distal end and the proximal end, the second catheter shaft further comprising a floating connector located at the proximal end thereof; a third catheter shaft having a proximal end and a distal end and being located within the second catheter lumen, extending from the distal end opening to the side opening, exiting through the side opening and extending proximally therefrom and exiting through the second proximal end opening of the first catheter shaft; the first catheter shaft, the second catheter shaft, and the third catheter shaft being in a substantially coaxial relationship at the distal end of the first catheter shaft; the first catheter shaft and the second catheter shaft being in a substantially coaxial relationship at the first proximal end opening of the first catheter shaft; and the first catheter shaft and the third catheter shaft being in a substantially coaxial relationship at the second proximal end opening of the first catheter shaft.

BRIEF DESCRIPTION OF THE FIGURES

FIG. 10 is a drawing of a delivery system according to the invention including a septal occluding device fully deployed;

FIG. 11 B is a schematic cross-section of a floating connector according to the invention; and FIG. 12 is a schematic cross-section of a floating connector according to the invention.

DETAILED DESCRIPTION OF PREFERRED EMBODIMENTS

Figure 1:
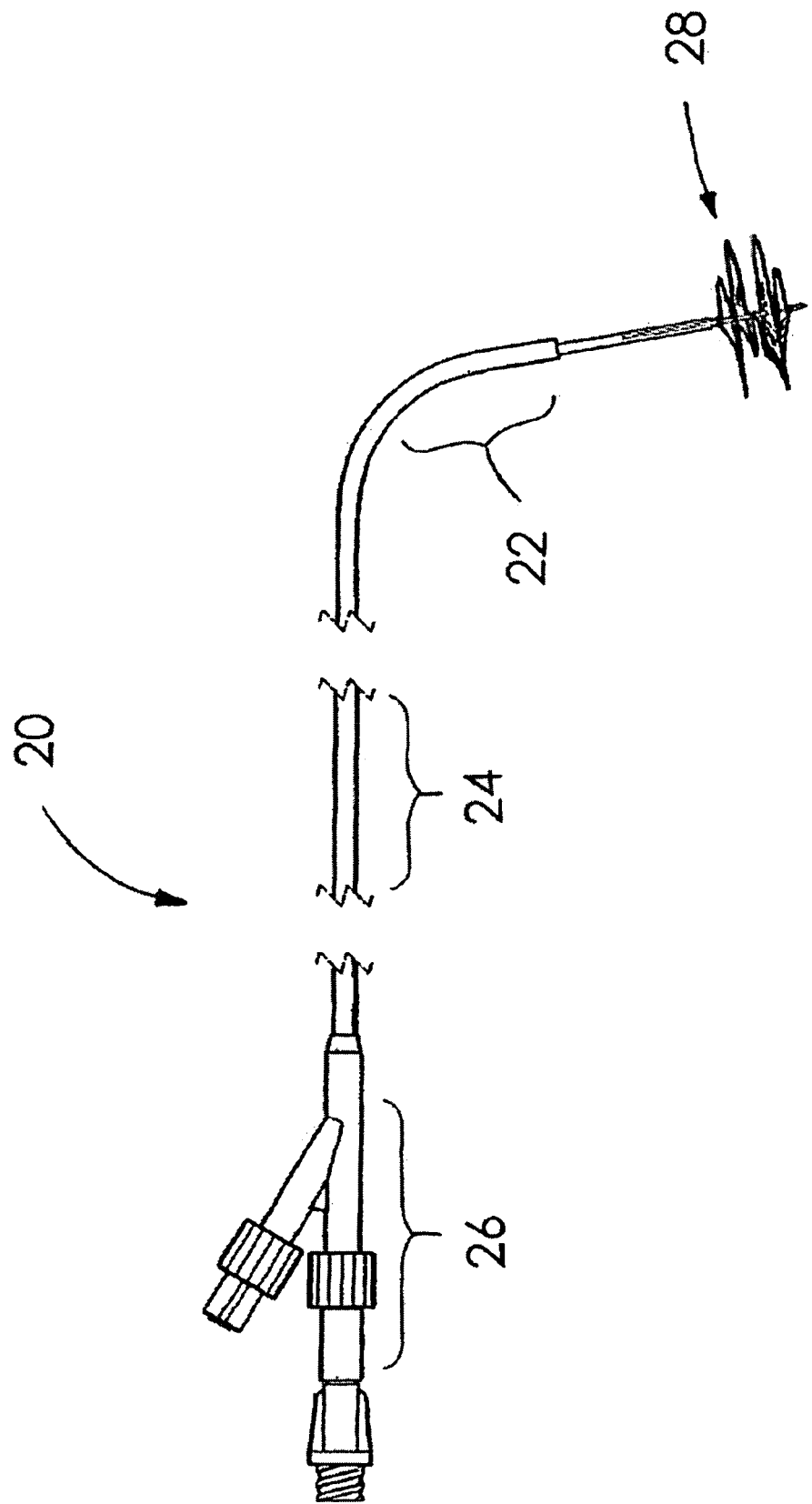
FIG. 1 is a drawing of a delivery system according to the invention including a deployed septal occluding device.

The current invention comprises an improved delivery system useful, for example, for delivering implantable devices. The delivery system of the invention can replace the three essentially coaxially arranged catheter components, discussed above.

Disclosed are novel delivery systems comprising: a first catheter shaft having a proximal end and a distal end, the proximal end having at least first and second openings, the distal end having at least one opening, and a lumen extending from the distal end opening to the at least first and second proximal end openings; a second catheter shaft having a proximal end and a distal end, at least a portion being located within the first catheter shaft lumen and extending from the first proximal end opening to the distal end opening, the second catheter shaft having a lumen extending from a distal end opening to at least a side opening in the second catheter shaft located between the distal end and the proximal end, the second catheter shaft further comprising a floating connector located at the proximal end thereof; a third catheter shaft having a proximal end and a distal end and being located within the second catheter lumen, extending from the distal end opening to the side opening, exiting through the side opening and extending proximally therefrom, and exiting through the second proximal end opening of the first catheter shaft; the first catheter shaft, the second catheter shaft, and the third catheter shaft being in a substantially coaxial relationship at the distal end of the first catheter shaft; the first catheter shaft and the second catheter shaft being in a substantially coaxial relationship at the first proximal end opening of the first catheter shaft; and the first catheter shaft and the third catheter shaft being in a substantially coaxial relationship at the second proximal end opening of the first catheter shaft.

Thus, the delivery system comprises three substantially coaxial catheters at the distal end of the first catheter, and a transitional mid-section wherein the third (i.e. the innermost) catheter exits the wall of the second catheter. The third catheter then extends proximally along the length of the second catheter in a collateral relationship to the second catheter and in an internal relationship to the first catheter. At the proximal end of the delivery system, the first catheter terminates with at least two proximal openings. For example, the proximal end of the first catheter can terminate in a "Y-arm" hub assembly, wherein the second catheter can exit through a first proximal opening and the third catheter can exit through a second proximal opening. In an aspect of the invention, the delivery system configuration can be described as having a first distal three-component, substantially coaxial section, a second transitional mid-section, and a third proximal section which comprises two coaxial sections.

The delivery system allows the user to maintain a close, hand-to-hand spacing while executing the delivery sequence. In addition, some of the delivery steps (required in the prior system) can be eliminated. Thus, the delivery system can be easier to use and can result in quicker delivery times.

In the improved delivery system configuration, the third (i.e., innermost) catheter exits through the wall of the second catheter. Therefore, at least the second catheter is constrained from rotating relative to the remaining two catheters. This can prevent damage to the catheters and also prevent the catheters from becoming entangled while manipulating the second and/or third catheter(s). To prevent the inadvertent rotation of the second catheter, for example during the attachment of connectors (e.g. luer fittings) onto the proximal end of the first catheter, an anti-rotation feature is incorporated with at least one of the second and third catheters. The connector of the present invention is free to rotate (or float) independently of the catheter shaft. Such a connector will hereinafter be referred to as a "floating connector." By floating connector it is meant that the connector is rotatably mounted about the catheter shaft while longitudinal constraint(s) is/are provided to allow the catheter to be pushed and pulled when grasping the floating connector. In an aspect of the invention the floating connector can be rotated 360 degrees or more without applying any significant torsional force to the catheter shaft. The floating connector is capable of being connected to the proximal end of the first catheter. In an aspect of the invention the floating connector is releasably attachable to the proximal end of the first catheter. In a further aspect of the invention the floating connector can be locked to the proximal end of the first catheter with an about 90 degree turn of the connector. Examples of suitable longitudinal constraints include, for example, the embodiments shown in FIGS. 11 A and B, and 12A and B, discussed in more detail below.

Specific aspects of the invention may be better understood with reference to the figures. Shown in FIG. 1 is a delivery system 20 according to the present invention, including HELEX™ septal occluder. The system 20 has a first distal three catheter, substantially coaxial section 22, a second transitional mid-section 24 and a third proximal dual coaxial section 26. Also shown is a formed HELEX™ septal occluder device 28 fully deployed from the distal three catheter section 22. Details relating to one delivery sequence of a HELEX™ septal occluder device are presented below. Of course, other septal occluding devices could be delivered using the delivery system of the invention. In an aspect of the invention the septal occluding device comprises polytetrafluoroethylene and metal wire. In a further aspect of the invention the polytetrafluoroethylene is expanded polytetrafluoroethylene and the wire is a nitinol wire.

Figure 2:
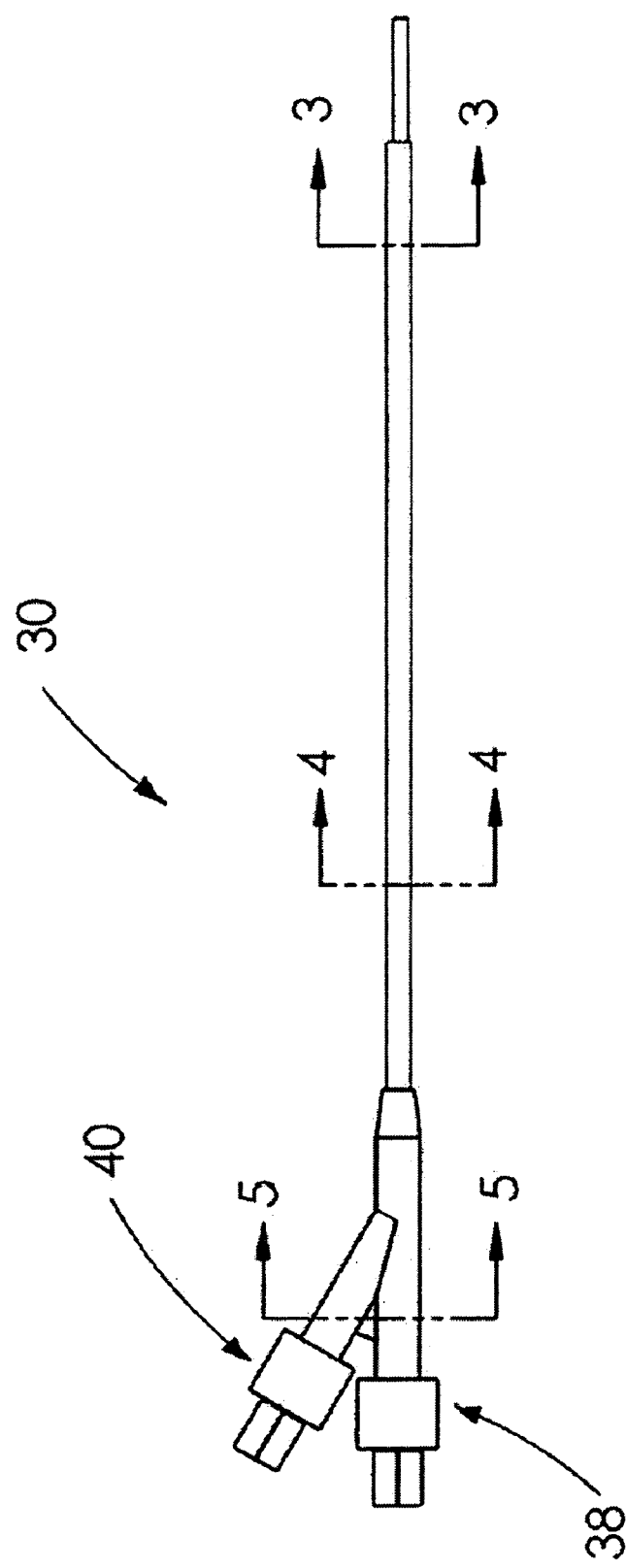
FIG. 2 is a drawing of a delivery system according to the invention.

One delivery system according to the present invention is displayed in FIG. 2. Shown is a general delivery system 30 defining three cross-sectional planes. A first cross-sectional plane 3 intersects a first distal, three-catheter, substantially coaxial section; a second cross-sectional plane 4 intersects a second transitional mid-section; while a third cross-sectional plane 5 intersects a third proximal dual coaxial section at the Y-arm hub assembly. Also shown are first proximal end 38 and second proximal end 40 of a Y-arm hub assembly.

Figure 3:
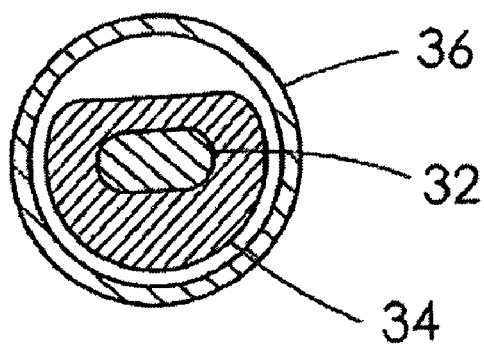
FIG. 3 is a schematic cross-section of the delivery system shown in FIG. 2, taken along lines 3-3.
Figure 4:
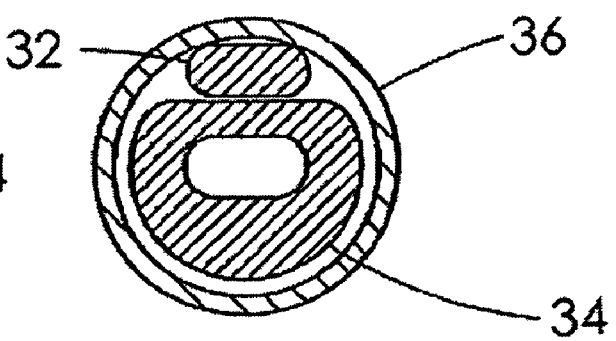
FIG. 4 is a schematic cross-section of the delivery system shown in FIG. 2, taken along lines 4-4.
Figure 5:
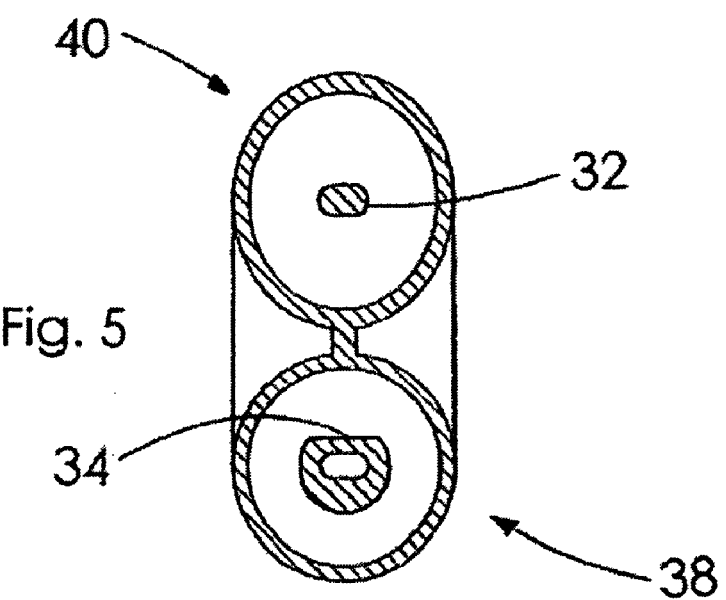
FIG. 5 is a schematic cross-section of the delivery system shown in FIG. 2, taken along lines 5-5.

FIGS. 3 through 5 show details of the system along these cross-sectional planes. Shown in FIG. 3 is cross-sectional end view of the three-catheter, substantially coaxial section comprising third (i.e., innermost) catheter 32 contained within second catheter 34 in a substantially coaxial and sliding arrangement. As used herein, a substantially coaxial arrangement is defined as at least one element contained within a second element wherein the elements do not necessarily share a common centerline, centroid or common axis. For example in FIG. 3 the centroid of the innermost catheter 32 is offset from the centroid of the second catheter 34. Both catheter components 32 and 34 are similarly contained within first catheter 36 in a substantially coaxial and sliding arrangement forming a three catheter substantially coaxial section. The distal ends of the second and third catheters can extend distally beyond the first catheter distal end. Moreover, the distal end of the third catheter can extend distally beyond the second catheter distal end.

Shown in FIG. 4 is a cross-sectional end view of a transitional mid-section showing the third catheter 32 oriented in a side-by-side or collateral relationship to the second catheter 34. The third and second catheters are in an "internal" relationship to and contained by the first catheter 36. The transitional mid-section can move from one point to another within the first catheter by pushing or pulling the second and/or third catheters.

FIG. 5 is a cross-sectional end view of a proximal, dual coaxial section of the Y-arm hub assembly. Shown is the second catheter 34 in a substantially coaxial relation with first proximal end 38 of the Y-arm hub assembly. Also shown is the third catheter 32 in a substantially coaxial relation with second proximal end 40 of the Y-arm hub assembly.

Figure 6:
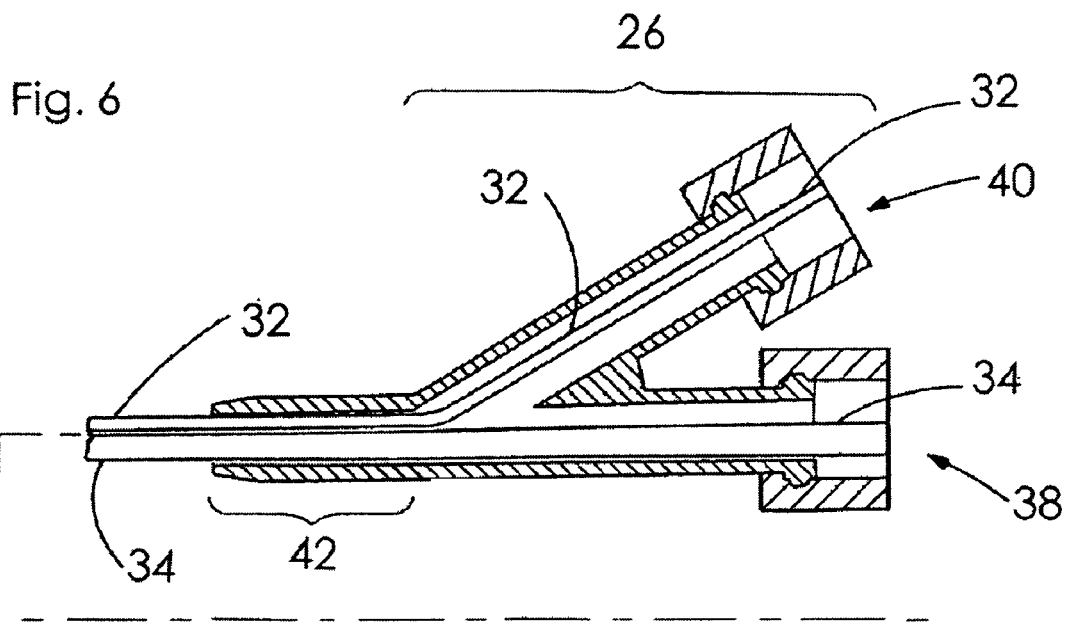
FIG. 6 is a schematic, longitudinal cross-section of section 26 of the delivery system shown in FIG. 1.

FIG. 6 is a partial longitudinal cross-section of a proximal dual coaxial section 26 shown here as a Y-arm hub assembly. Shown is a first proximal end 38 terminating with a first proximal opening. Second catheter 34 extends, in a coaxial relationship, through the first proximal. opening. Also shown is second proximal end 40, terminating with a second proximal opening. Third catheter 32 extends, in a coaxial relationship, through the second proximal opening. These catheter components form a dual coaxial section at the Y-arm hub assembly. As shown, along the distal portion 42 of the Y-arm hub assembly, the third catheter 32 is oriented in a collateral relationship to the second catheter 34 (as also depicted in FIG. 4).

Figure 7:
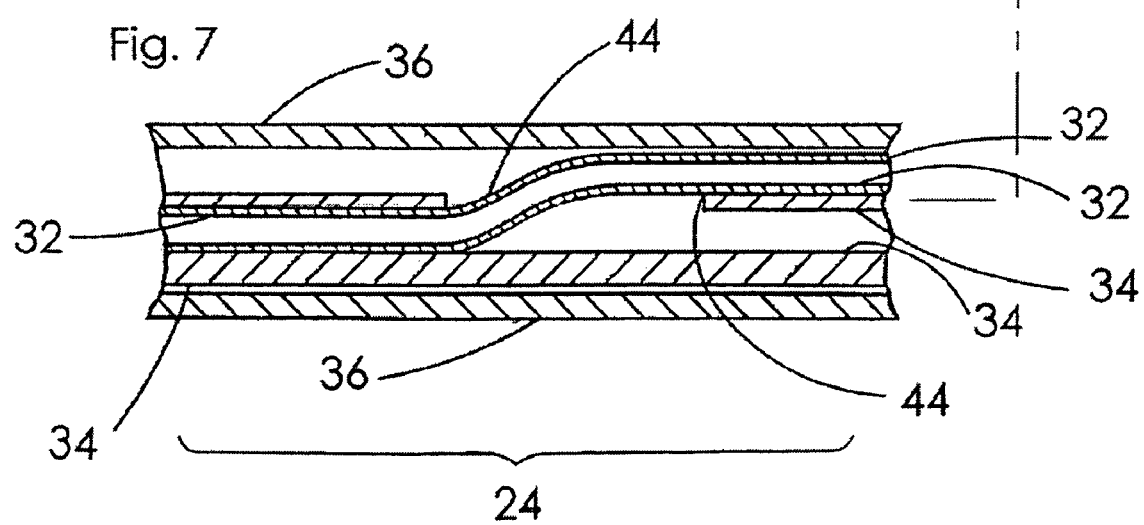
FIG. 7 is a schematic, longitudinal cross-section of section 24 of the delivery system shown in FIG. 1.

The third 32 and second 34 catheters extend distally from the Y-arm hub assembly in a collateral relationship to a transitional mid-section 24, as shown in partial longitudinal cross-section in FIG. 7 (scale enlarged relative to FIG. 6). Shown in FIG. 7 is a third innermost catheter 32 protruding through a port or opening 44 in the wall of the second catheter 34. The third catheter 32 therefore transitions from a collateral relationship to a substantially coaxial relationship relative to the second catheter 34. Both catheters 32 and 34 are similarly contained within first catheter 36 in a substantially coaxial arrangement, forming a three component substantially coaxial distal section.

Since the third innermost catheter 32 exits the wall of the second catheter 34, the second catheter is ideally constrained from rotating relative to the remaining two catheters. To prevent the inadvertent rotation of the second catheter 34, for example during the attachment of a connector onto the first proximal end 38 of the Y-arm hub assembly, a floating connector is provided to the proximal end of the second catheter.

The floating connector is free to rotate independently of the catheter shaft 34. Further details relating to the anti-rotation features of the floating connector are presented below.

Figure 8:
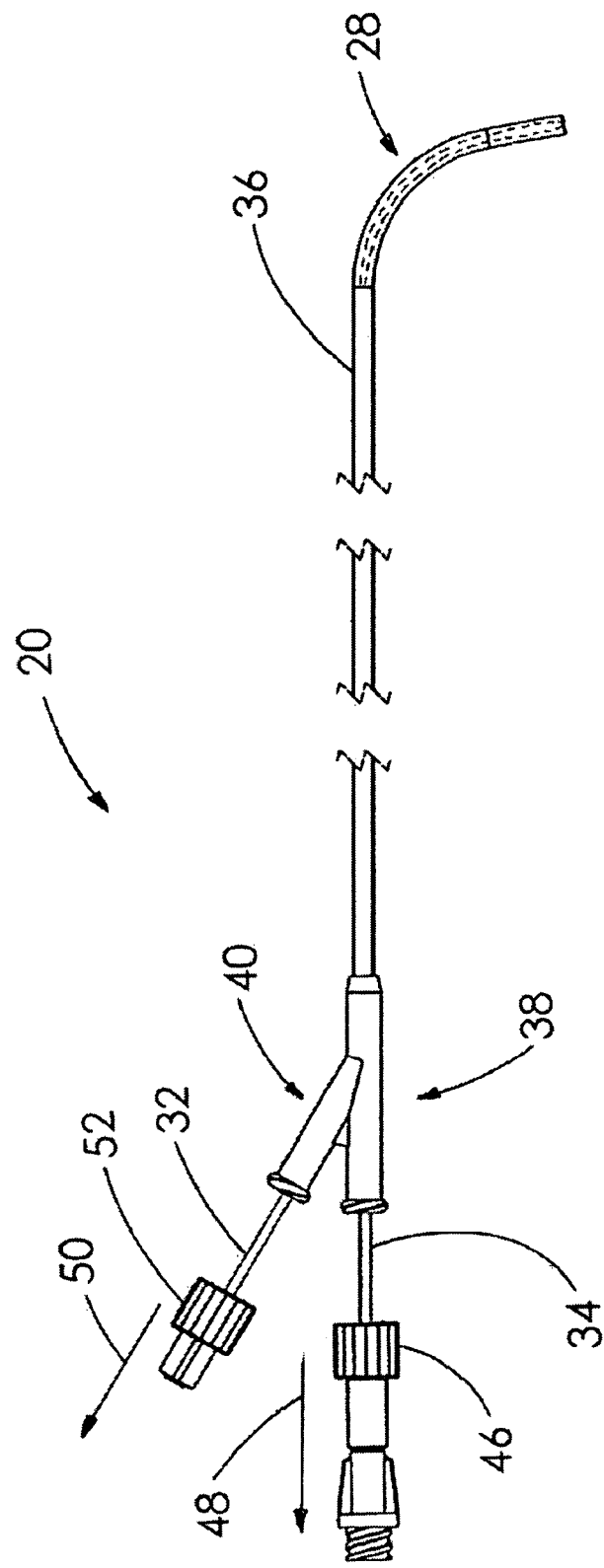
FIG. 8 is a drawing of a delivery system according to the invention including a septal occluding device loaded in the delivery system.
Figure 9:
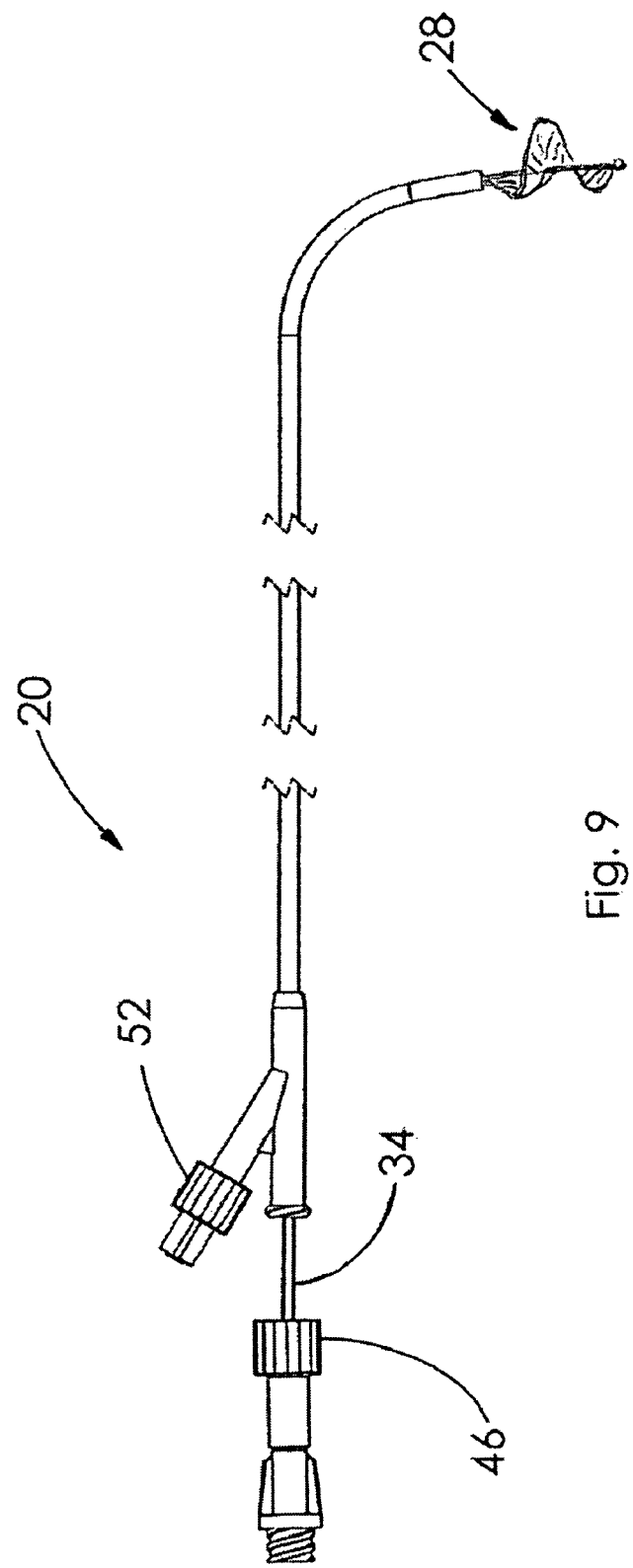
FIG. 9 is a drawing of a delivery system according to the invention including a septal occluding device partially deployed therefrom.

To illustrate the use of one delivery system according to the present invention, FIGS. 8 through 10 show various stages of a HELEX™ septal occluder deployment sequence. Shown in FIG. 8 is a HELEX™ septal occluder 28 loaded into delivery system 20. Such a system can typically be packaged for shipment in the configuration shown in FIG. 1 (that is with the HELEX™ septal occluder in a deployed state and floating connectors connected to first and second proximal ends of the first catheter. Particularly useful floating connectors can be of the "luer" type connector. The description will exemplify such luer type connectors. However, the skilled artisan will understand the various alternative embodiments that can be used. Starting with the configuration shown in FIG. 1, the floating male luer 46 located on the proximal end of the second catheter 34 is unlocked from the first proximal end of the first catheter 36 by a counter-clockwise rotation. This counter-clockwise rotation is not translated to the second catheter 34 due to the design of the floating luer 46. The HELEX™ septal occluder 28 is pulled into the first catheter 36 of the delivery system 20 by pulling the floating luer 46 along with the second catheter 34 in a proximal direction 48. When approximately 90% of the HELEX™ septal occluder 28 is pulled into the first catheter 36, the second floating luer 52 located on the proximal end of the third catheter 32 is unlocked from the second proximal end of the first catheter 36 by a counter-clockwise rotation. This counter-clockwise rotation is not translated to the third inner catheter 32 due to the design of the floating luer 52. It should be understood that a floating connector for the third catheter is an optional embodiment, as preventing twisting or rotation of the third catheter is not as critical as preventing twisting or rotation of the second catheter. However, use of the floating connector on the third catheter can still be desirable. The remaining 10% of the HELEX™ septal occluder is then pulled into the first catheter 36 by pulling the floating male luer 46 along with the second catheter 34 in a proximal direction 48. The third inner catheter 32 is forced to move in the proximal direction 50 as the second catheter 34 is pulled in the proximal direction 48. FIG. 8 depicts a HELEX™ septal occluder 28 fully loaded into the first catheter 36 and ready for use by the physician.

The delivery system 20 with the fully loaded device is then advanced through the vasculature and positioned, for example, across a septal defect. The HELEX™ septal occluder 28 can then be deployed by translating the third and second catheters relative to the first catheter, in a series of push-pull motions.

Shown in FIG. 9 is a HELEX™ septal occluder 28 in a partially deployed state. The floating luers 46 and 52 can be locked and unlocked during the delivery sequence without imparting a twisting motion to the third and second catheters. The push-pull delivery sequence is continued until the HELEX™ septal occluder 28 is fully deployed as shown in FIG. 10 with a portion of the device located on each side of the septal defect, thus occluding the defect. As will now be appreciated, the improved delivery system of the present invention allows the user to maintain a close hand-to-hand spacing throughout the delivery sequence.

Figure 11A:
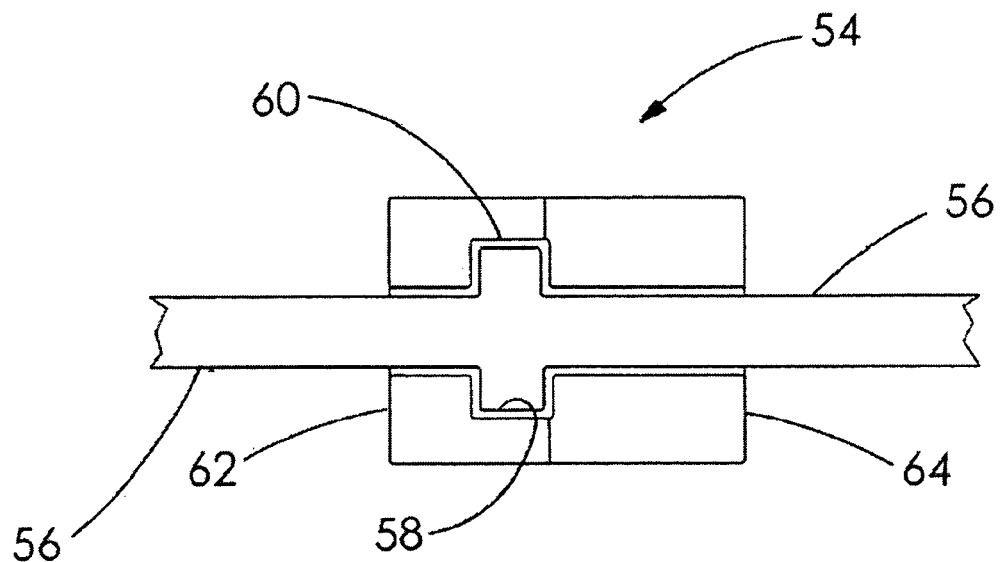
FIG. 11 A is a schematic cross-section of a floating connector according to the invention.

Further, exemplary description of the floating connectors will now be presented. An aspect of the invention comprises a connector that is free to rotate relative to a catheter shaft without applying torsional force to the catheter shaft. The connector is therefore free to rotate independently of the catheter shaft. Thus, inadvertent twisting of the catheter shaft can be avoided while connecting the connector to the proximal end of another catheter. Exemplary configurations include floating luer-type connectors. Examples of such floating luers are shown in schematic in FIGS. 11A and 11B. Shown in FIG. 11A is a general floating luer 54 having an internal containment groove 60. Also shown is a general catheter 56 that includes at least one protrusion, in this case ring 58. Protrusion or ring 58 can be an integral part of the catheter shaft, or it can be joined to the shaft using, for example, suitable adhesives. The ring 58 is contained in the luer internal containment groove 60. Thus, the ring 58 and containment groove 60 act as longitudinal constraint to allow the catheter 56 to be pushed and pulled while grasping floating luer 54. The luer can be assembled onto the catheter 56 by inserting and joining first and second luer portions 62, 64 together by an adhesive or any other suitable attachment means. The joined luer portions 62, 64 are free to rotate relative to the catheter 56.

Figure 11B:
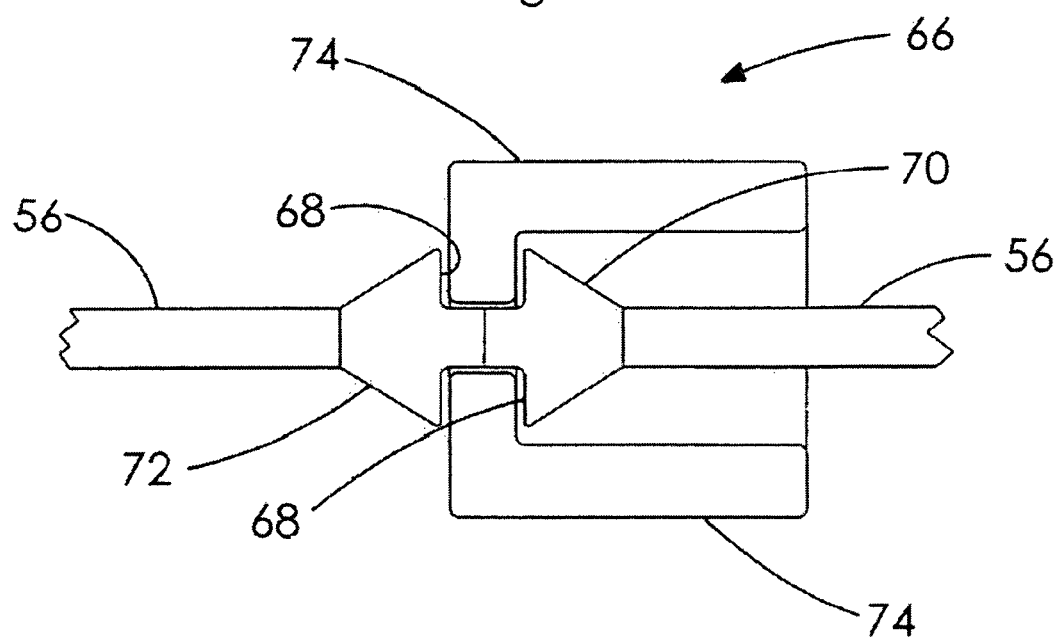

An alternate floating luer configuration is shown in FIG. 11B. Shown is a general floating luer 66 longitudinally constrained by an external groove 68 formed by two opposing catheter stop components 70, 72. The two catheter components can be attached to the catheter shaft 56, forming a groove 68, or the catheter can be molded in this configuration. The luer 74 is free to rotate relative to the catheter shaft 56. The catheter 56 can be longitudinally translated by pushing or pulling on the luer 74.

A further embodiment of a floating luer assembly is depicted in partial cross-section in FIG. 12. This configuration is similar in function to that shown in FIG. 11 B and is similar to the luer numbered 52 in FIGS. 8 through 10. Shown in FIG. 12 is a floating luer 52 with catheter 32. The catheter 32 is retained within the luer 52 by a proximal stop 76 and a distal stop 78. The proximal stop 76 and the distal stop 78 can be attached to the catheter 32 by an adhesive or any other suitable attachment means. The floating luer 52 is free to rotate relative to the catheter shaft 32. The catheter can be longitudinally translated by pushing or pulling on the luer 52.

A still further embodiment of a floating luer assembly is similar in function to that shown in FIG. 11B and is similar to the luer numbered 46 in FIGS. 8 through 10. Specifically, the catheter is retained within the luer by a proximal stop and a distal stop. The proximal stop and the distal stop can be attached to the catheter by an adhesive or any other suitable attachment means. The luer is free to rotate relative to the catheter shaft. The catheter can be longitudinally translated by pushing or pulling on the luer. The proximal stop is a female luer fitting. This female luer allows the attachment of other components such as male luers, syringes, flushing instruments, etc.

Various materials that can be used to fabricate the individual components of the delivery system are well within the purview of the skilled artisan.

While particular embodiments of the present invention have been illustrated and described above, the present invention should not be limited to such particular illustrations and descriptions. It should be apparent that changes and modifications may be incorporated and embodied as part of the present invention within the scope of the following claims.

The invention claimed is:

1. A delivery system comprising:
   a first catheter shaft having a proximal end and a distal end, the proximal end having a hub component having at least first and second proximal end openings, the distal end having at least one opening, and a single lumen extending from the distal end opening to the proximal end;
   a second catheter shaft having a proximal end and a distal end, at least a portion being located within the first catheter shaft lumen and extending from the first proximal end opening of the hub component to the distal end opening of the first catheter shaft, the second catheter shaft having a lumen extending from a distal end opening to at least a side opening in the second catheter shaft located between the distal end and the proximal end of the second catheter shaft, the second catheter shaft further comprising a floating connector located at the proximal end thereof;

a third catheter shaft having a proximal end and a distal end and being located within the second catheter lumen, extending from the distal end opening to the side opening of the second catheter shaft, exiting through the side opening of the second catheter shaft and extending proximally therefrom and exiting through the second proximal end opening of the hub component;

the first catheter shaft, the second catheter shaft, and the third catheter shaft being in a substantially coaxial relationship at the distal end of the first catheter shaft;

the first proximal end of the hub component and the second catheter shaft being in a substantially coaxial relationship at the first proximal end opening of the hub component;

the second proximal end of the hub component and the third catheter shaft being in a substantially coaxial relationship at the second proximal end opening of the hub component, and further comprising a septal occluding device, which can be deployed by translating the third and second catheters relative to the first catheter, in a series of push-pull motions.

2. The delivery system of claim 1, wherein a floating connector is located at the proximal end of the third catheter shaft.

3. The delivery system of claim 2, wherein the floating connector located at the proximal end of the second catheter is a luer-type connector.

4. The delivery system of claim 2, wherein the floating connector located at the proximal end of the third catheter is a luer-type connector.

5. The delivery system of claim 1, wherein the hub component comprises a Y-shaped hub assembly.

6. The delivery system of claim 1, wherein the septal occluding device comprises polytetrafluoroethylene.

7. The delivery system of claim 6, wherein the polytetrafluoroethylene comprises expanded polytetrafluoroethylene.

8. The delivery system of claim 6, wherein the septal occluding device further comprises metal wire.

9. The delivery system of claim 8, wherein the wire comprises nitinol.

10. The delivery system of claim 7, wherein the septal occluding device further comprises metal wire.

11. The delivery system of claim 10, wherein the wire comprises nitinol.

12. The delivery system of claim 1, wherein the second catheter shaft is constrained from rotating relative to the first and third catheter shafts.

13. The delivery system of claim 12, wherein the second catheter shaft is constrained from rotating by the floating connector located at the proximal end thereof.

* * * * *